United States Patent [19]
Ouvrard

[11] 4,024,753
[45] May 24, 1977

[54] METHOD AND APPARATUS FOR THE CONTINUOUS AUTOMATIC ANALYSIS OF THE CRYSTALLIZATION POINT OF LIQUID SUBSTANCES

[75] Inventor: Paul Ouvrard, Saint Nazaire, France

[73] Assignee: Societe Anonyme dite: Antar Petroles de l'Atlantique, Paris, France

[22] Filed: Mar. 11, 1976

[21] Appl. No.: 665,967

Related U.S. Application Data

[63] Continuation-in-part of Ser. No. 505,645, Sept. 13, 1974, Pat. No. 3,945,243.

[30] Foreign Application Priority Data

Mar. 21, 1975 France .............................. 75.08934

[52] U.S. Cl. .................................. 73/17 R; 73/61.4
[51] Int. Cl.² ........................................ G01N 25/04
[58] Field of Search ........................... 73/17 R, 61.4

[56] References Cited
UNITED STATES PATENTS

| | | | |
|---|---|---|---|
| 2,591,084 | 4/1952 | Martin | 73/17 R |
| 2,750,433 | 6/1956 | Tourneau et al. | 73/17 R X |
| 2,997,874 | 8/1961 | Billuris et al. | 73/17 R X |
| 3,143,876 | 8/1964 | Wallgren | 73/17 R |
| 3,213,668 | 10/1965 | Thompson | 73/17 R |
| 3,577,765 | 5/1971 | Bertoglio et al. | 73/17 R |
| 3,872,710 | 3/1975 | Louvel | 73/17 R |

*Primary Examiner*—Richard C. Queisser
*Assistant Examiner*—Joseph W. Roskos

*Attorney, Agent, or Firm*—Hammond & Littell

[57] ABSTRACT

The method consists of passing the substance to be analyzed through a measuring circuit at a constant flow rate, the temperature therein being maintained at a value sufficiently below the assumed crystallization point of the substance. Heating means are provided along the flow path of the liquid substance in said circuit. The substance in the course of cooling is kept in contact with an isomorphous crystalline material. The heating means is automatically turned on and off respectively at two characteristic temperatures, which are detected by measuring the pressure drop or difference of pressure of the substance at the inlet and at the outlet of the measuring circuit, variations of the pressure drop being effected as a function of temperature. The values thus measured of the pressure drop are utilized as control data for respectively turning on and off the heating means when the temperature of the substance at the outlet reaches one of its two characteristic values, the first corresponding to the crystallization temperature level, while the other corresponds to a temperature sufficiently above said crystallization point. The temperature of the substance at the outlet of the circuit is continuously recorded, which constitutes a value representing the crystallization point of the substance. The method and the apparatus are particularly useful for determining the crystallization point of benzene, of paraxylene or of orthoxylene automatically and continuously.

5 Claims, 5 Drawing Figures

METHOD AND APPARATUS FOR THE CONTINUOUS AUTOMATIC ANALYSIS OF THE CRYSTALLIZATION POINT OF LIQUID SUBSTANCES

REFERENCE TO A PRIOR APPLICATION

This application is a continuation-in-part of my copending application Ser. No. 505,645 filed Sept. 13, 1974, Now U.S. Pat No. 3,945,243.

BACKGROUND OF THE INVENTION

1. Field of the Invention

The present invention relates to a method and apparatus for the continuous automatic analysis of the crystallization point of liquid substances, especially of aromatic hydrocarbons.

2. Description of the Prior Art

A method and an apparatus for the automatic continuous analysis of the filterability point of liquid substances, in particular of gas-oils during manufacture, is described in U.S. patent application Ser. No. 505,645 filed by applicant on Sept. 13, 1974.

The method consists of passing a substance to be analyzed through a measuring circuit at a constant flow rate, the temperature therein being maintained at a value sufficiently below the assumed filterability point of the substance, heating means being provided along the flow path of the liquid substance in said circuit, and automatically turning on and off said heating means respectively at two characteristic temperatures detected by measuring the pressure drop or difference in pressure of the substance at the inlet and at the outlet of the circuit, the variation of said pressure drop being effected as a function of temperature, the values thus measured of the pressure drop being utilized as control data for respectively turning on and off the heating means, when the temperature at the outlet of the substance reaches one of the two characteristic temperatures, the first corresponding to a temperature slightly below the filterability point, whilst the other corresponds to a temperature sufficiently above said filterability point, and in that the temperature of the substance at the outlet of the circuit is recorded continuously, which temperature constitutes a representative value of the filterability point of the substance.

A preferred embodiment of the apparatus for carrying out the aforementioned method comprises a measuring circuit constituted by a capillary tube of stainless steel traversed by the substance to be analyzed, whose flow rate is kept constant by a small volumetric pump, the capillary tube having a large portion of its length immersed in a cooling liquid bath contained in a measuring well, the inlet and the outlet of the capillary tube in the well being connected, outside of the well, to two electrical leads of which one is directly connected to the power supply whilst the other is connected to differential pressure-responsive switching means, mounted between the inlet and the outlet of the capillary tube, whilst a thermosensitive element is positioned at the outlet of the measuring well along the flow path of the substance to be analysed and is connected to a recording device.

The aforementioned patent application also describes a method and an apparatus for the continuous measurement of the filterability temperature limit, the filterability point corresponding to the appreciable diminution of the flowability of a gas-oil when the temperature drops.

Devices have also already been described, enabling the determination of the crystallization temperature of a liquid. Reference may notably be made to U.S. Pat. No. 3,577,765, which relates to a method and an apparatus for determining automatically the crystallization temperature of a flowing liquid and more particularly of aqueous solutions, for example of sodium benzenesulfonate whose crystallization is not of the "clean" type, that is to say it manifests an increase in viscosity of the cooled liquid stream.

Such a method is not suitable for substances of high purity, such as, for example, benzene, paraxylene, or orthoxylene, since these substances having a crystallization of the "clean" type, exhibit a random undercooling phenomenon, described in more detail in the description which follows, and this phenomenon is a handicap for the automatic continuous analysis of the crystallization point.

OBJECTS AND GENERAL DESCRIPTION OF THE INVENTION

It is therefore an object of the present invention to provide an improved method and apparatus for the automatic continuous analysis of the crystallization point of liquid substances.

It is a further object of the present invention to provide a method and an apparatus specially adapted to the automatic continuous analysis of the crystallization point of substances with crystallization of the "clean" type.

It is another object of the present invention to provide a method and an apparatus for overcoming the abovementioned drawbacks of the prior art method and apparatus, notably in that it overcomes the phenomenon of random undercooling or supercooling of a substance with "clean" crystallization in the course of cooling.

In cold testing, gas-oils undergo changes of state. It is therefore a further object of the present invention to provide a method and an apparatus well adapted to the continuous measurement and definition of the characteristics of a gas-oil.

It is a further object of the present invention to provide a method and an apparatus for the continuous measurement of the crystallization point of a gas-oil and more particularly of an aromatic hydrocarbon.

Other objects and advantages of the method and apparatus according to the present invention will emerge from the description which follows.

According to the invention, in its most general form, there is provided a method for the automatic continuous analysis of the crystallization point of liquid substances, particularly of aromatic hydrocarbons, characterized in that it consists of passing a constant flow rate of the substance to be analysed through a measuring circuit, whose temperature is kept at a value sufficiently below the assumed crystallization point of said substance, heating means being provided in the flow path of the liquid in said circuit, in that the liquid substance to be analyzed is kept in the course of cooling in contact with an isomorphous crystalline material, and in that said heating means are automatically turned on and off respectively at two characteristic temperatures detected by measuring the pressure drop or pressure difference of the substance at the inlet and at the outlet of the measuring circuit, the variation of said pressure drop being effected as a function of temperature, the valves thus measured of the pressure drop being utilized as control data for turning on and off respectively the heating means, when the temperature at the outlet of the substance reaches one of its two characteristic values, the first corresponding to the crystallization temperature level whilst the other corresponds to a temperature sufficiently above said crystallization point, and in that the temperature of the substance at the outlet of the circuit is recorded continuously, which constitutes a representative value of the crystallization point of the substance.

According to another aspect of the invention, in its most general form, there is provided an apparatus for carrying out the aforesaid method, which apparatus comprises a measuring circuit constituted by a stainless steel capillary tube traversed by the substance to be analysed, of which the flow rate is maintained constant by a small volumetric pump, the capillary tube having a large portion of its length immersed in a cooling liquid bath contained in a measuring well, the bottom of the latter being arranged in the form of a liquid-tight crystals chamber which contains an isomorphous crystalline material, a short portion of the capillary tube extending through said chamber, the isomorphous material being in contact with the substance to be analysed, by means of an opening formed in the portion of the tube situated in said chamber, the inlet and the outlet of the capillary tube in the well being connected externally of the well to two electrical leads of which one is directly connected to the differential pressure-responsive switching means, mounted between the inlet and the outlet of the capillary tube, whilst a thermosensitive element is positioned at the outlet of the measuring well on the flow path of the substance to be analysed and is coupled to a recorder.

BRIEF DESCRIPTION OF THE DRAWINGS

In order that the invention may be more fully understood, several embodiments of the method and apparatus according to the invention are described below with reference to the accompanying drawings, given of course, purely by way of non-limiting example. In the drawings.

DESCRIPTION OF PREFERRED EMBODIMENTS

There is of course a relative similarity for gas-oils in the course of cooling, between the change of state corresponding to the filterability point and the crystallization.

However, it must be noted that there is difference in crystallizing substances of the "pasty" type and those with "clean" crystallization.

Figure 1:
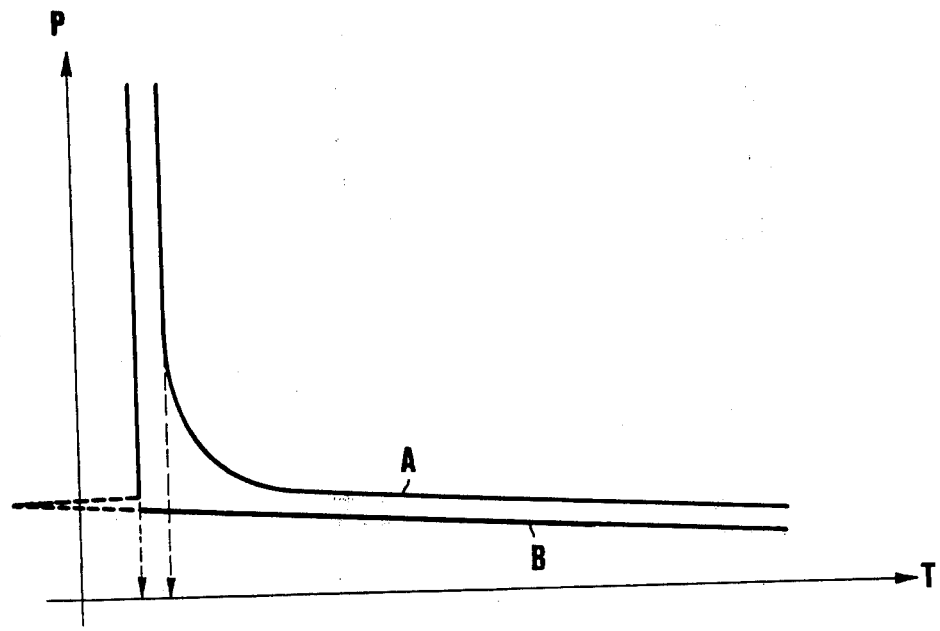
FIG. 1 is a graph by way of explanation.

Referring to FIG. 1 of the accompanying drawings, the difference between "pasty" type crystallization and "clean" type crystallization will now be defined.

FIG. 1 is a graph showing the known temperature/pressure drop relationship in the case of a gas-oil.

Curve A shows the development of the pressure drop in a circuit traversed by a gas-oil in the course of cooling, this gas-oil having progressive crystallization of the "pasty" type.

Curve B shows the development of the pressure drop in a circuit traversed by a gas-oil in the course of cooling, this gas-oil having a "clean" crystallization. This "clean" crystallization is the case for aromatic substances such as benzene, paraxylene and orthoxylene.

The dashed portion of curve B corresponds to the random undercooling which mostly precedes any clean crystallization. This phenomenon is a particularly constraining handicap in carrying out continuous analysis, but it is possible to eliminate the risk thereof completely by maintaining the liquid in the course of cooling in contact with an isomorphous crystalline material, that is to say of the same system of crystallization.

In the method according to the invention, generally, the flow rate of the substance to be analysed is kept constant, although the variation of the pressure drop is measured progressively as the temperature of the circulating substance drops, this substance being kept in contact with an isomorphous crystalline material in the part where its crystallization takes place.

Figure 2:
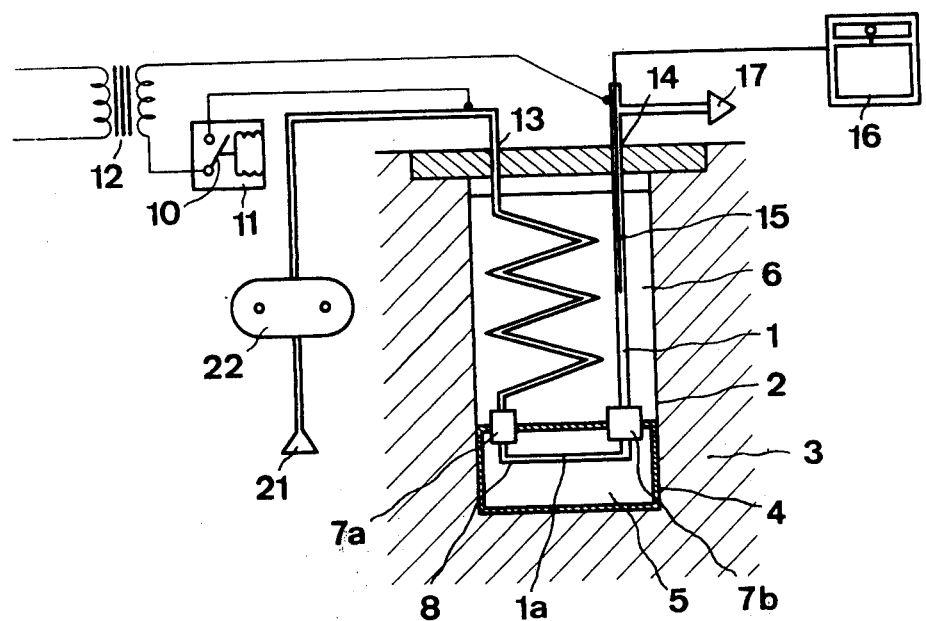
FIG. 2 is a diagram of an embodiment of the apparatus according to the invention.

FIG. 2 shows diagrammatically an embodiment of the apparatus according to the invention.

The analyser of the crystallization point comprises a measuring circuit constituted by a capillary tube of stainless steel.

This capillary tube 1 is traversed by a substance to be analysed supplied at 21 and propelled by a volumetric pump 22 situated downstream. The tube 1 passes into a measuring well 2. This measuring well 2 is a cavity of small volume formed in a solid mass 3 of steel. This measuring well comprises a fluid-tight chamber 4 in its lower part, said chamber 4 containing an isomorphous crystalline material 5, that is to say of the same system of crystallization as the substance to be analysed, a rhombic pyramid system, for example, if the substance to be analysed is benzene. The remaining part of the measuring well 2 is filled with a nonfreezable product 6.

The solid steel mass 3 comprises means connected to a cooling unit and is heat-insulated.

The capillary tube 1 has an outer diameter of 1.5 mm and an inner diameter of about 1.2 mm, and it is shaped so that it offers a fairly large surface in the measuring well 2 before the entry of said tube 1 into the crystals chamber 4; the tube 1 may for example have a substantially helicoidal shape. The capillary tube 1 penetrates the crystals chamber 4 through a fluid-tight and electrically insulating barrel 7a and reemerges therefrom through a barrel 7b identical with the barrel 7a. The portion 1a of the capillary tube 1 passing into the crystals chamber 4 comprises a longitudinal opening 8 formed throughout the length of a generator of this portion of tube 1a. This opening 8 thus permits the liquid stream circulating in the capillary tube to be placed in communication with the isomorphous material 5, for example, benzene, stored in the chamber 4.

The capillary tube 1 has a length of about 100 cm and represents an electrical resistance of about 1 ohm. The inlet and outlet connections of the tube 1 are formed as insulating joints and are connected, through a switch 10, associated with differential pressure-sensing switch means 11, to a potential difference 12 (mains).

The differential pressure-sensing means 11 is mounted between the inlet 13 of the tube of the measuring circuit on the side of its high pressure connection and the outlet 14 of the measuring circuit on the side of its low pressure condition.

On the side of the outlet 14 of the measuring well, a thermosensitive element 15 dips into the outlet section of the capillary tube 1. This element 15 is constituted by a platinum resistance of 100 Ω at 0° C, technically known as "pyrothenax"; its outer end is connected to a continuous temperature recorder 16.

At its outlet 14 from the measuring well 2, the capillary tube 1 is extended perpendicularly to the thermosensitive element 15 and its end is provided with a drain 17.

The dynamic behaviour of the whole of the apparatus will now be described.

At the inlet of the circuit, by means of the volumetric pump 22, the constant flow rate of the substance to be analysed is ensured, which permits continuous circulation of the substance in the capillary tube 1.

The analysis unit or measuring well 2 is kept at 0° C and, the circulation being established in the capillary tube 1, the sequence of analysis cycles occurs in the manner described below.

The temperature of the substance to be analysed 5, for example benzene, standing in the chamber 4, drops rapidly since this chamber is in direct thermal contact with the bottom of the cooling well. After a possible, but single, initial overcooling, the product 5 crystallizes in the chamber 4. The liquid stream circulating in the capillary tube 1 is hence in physical contact with iso-morphous crystals, which avoids over cooling during its crystallization. In fact, as soon as the liquid benzene flowing in the tube, as a result of its progressive cooling, reaches crystallization temperature, there is a solidification of the capillary, or of a considerable portion of the latter without the appearance of a random under cooling phenomenom preceding "clean" crystallization. The stopping of the flow which results from the solidification of the capillary causes a rise in pressure at the inlet of the capillary and results in closing the pressure-sensitive switch 10; the differential pressure-sensing means 11 connected to this capillary 1 then actuates the starting up of the reheating sequence by applying an alternating potential difference to the terminals of the capillary 1, which then behaves as a heating resistance.

The rise in temperature of the whole of the capillary circuit causes fusion of the crystals occurring therein, thus freeing the flow in the capillary, which permits instantaneous return to the initial pressure and thus causes the stopping of the heating.

The relatively large amount of crystals 5 immobilized in the chamber 4, and the fact that the latter are kept at a temperature sufficiently below their melting point, enables their permanence to be ensured, only the layers surrounding the capillary being liable to successive fusions and crystallization. Liquid/solid physical contact is thus ensured constantly inspite of the slight mobility of the transistion zone.

The sequences of analyses then follow, according to the procedure described above, at the rate of about three per minute. This frequency of recurrence is hence sufficient to permit the analysis to be compared with continuous analysis.

The development of the temperature thus recorded by the device 16 then presents itself in the form of a saw-tooth, whose lower crests locate accurately the successive values of the crystallization temperatures.

The envelope curve of these low crests enables the development of the latter to be followed, although it is of course possible to insert in the recording channel a memory device enabling only the continuous tracing of this low envelope to be recorded.

The apparatus according to the invention has been utilized for the continuous analysis of the crystallization point of benzene.

Figure 3:
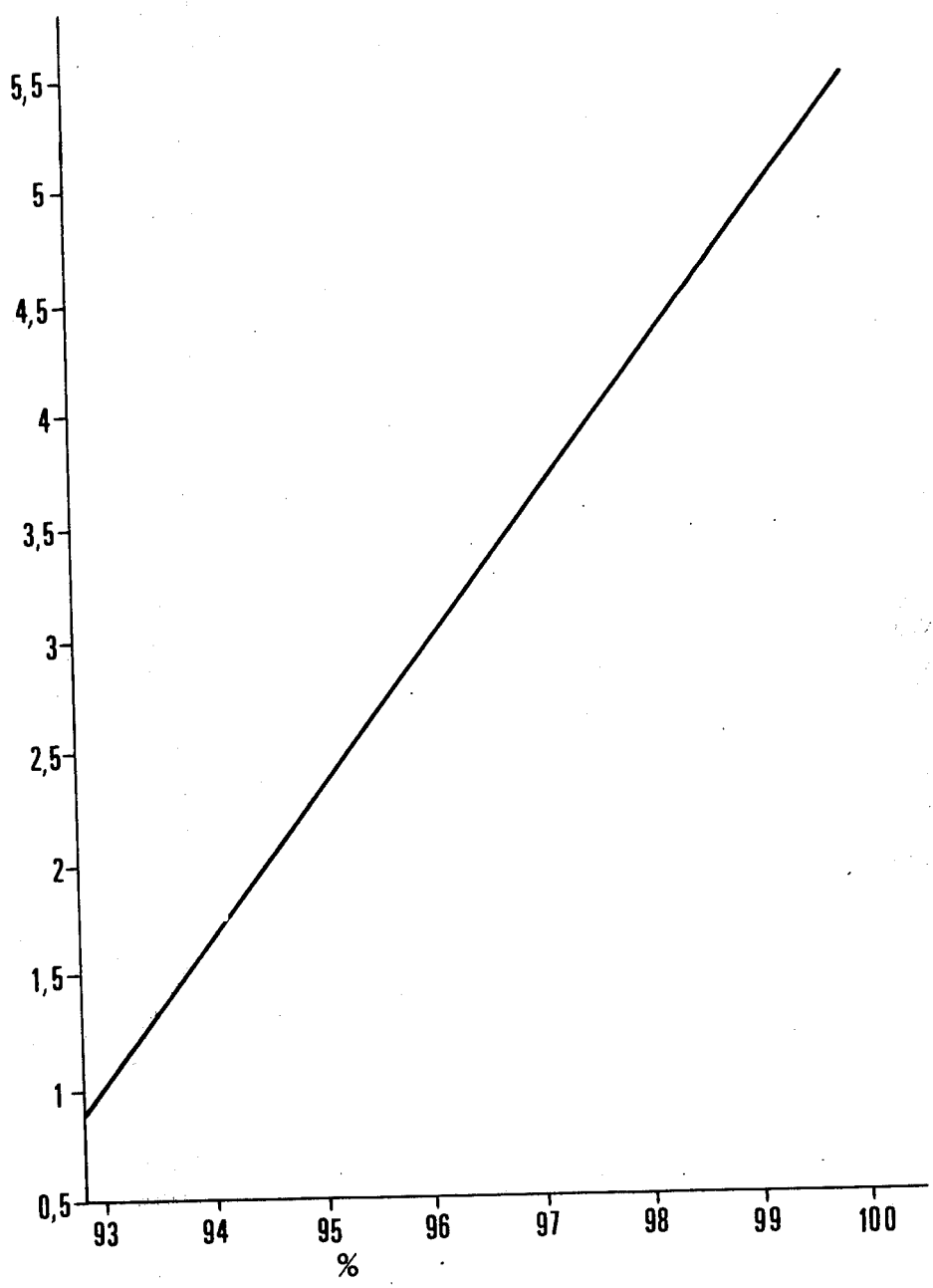
FIG. 3 is a graph showing the temperature/purity relationship for benzene.

Of course, a relationship exists between the crystallization temperature and the purity of the benzene, whose graphic representation is shown in FIG. 3. This curve represents the crystallization temperature in degrees centigrade as ordinate, as a function of the purity of the benzene in % as abscissea.

The graph of FIG. 3 has been calculated from cryoscopic constants according to the formula:

$$\text{Log}_{10} P = 2.00000 - (A/2.3026)(t_{po} - t_p)[1 + B(t_{po} - t_p)]$$

where $P$ = percentage of moles of benzene
$A$ = 0.01523 molar fraction per degree
$B$ = 0.0032 molar fraction per degree
$t_{po}$ = 5.333 ± 0.010° C
$t_p$ = crystallization point in °C of the impure benzene.

By means of the apparatus according to the invention, table I given below has been recorded which enables the temperature of crystallization/purity of benzene relationship to be established.

TABLE I

| PURITY OF THE BENZENE AS A FUNCTION OF THE CRYSTALLIZATION POINT | | | |
|---|---|---|---|
| Crystallization point ° C | % Benzene | Crystallization point ° C | % Benzene |
| 1.0 | 93.2 | 3.5 | 96.9 |
| 1.1 |  | 3.6 | 97.1 |
| 1.2 | 93.5 | 3.7 | 97.2 |
| 1.3 | 93.7 | 3.8 | 97.4 |
| 1.4 | 93.8 | 3.9 | 97.5 |
| 1.5 | 94.0 | 4.0 | 97.7 |
| 1.6 | 94.1 | 4.1 | 97.8 |
| 1.7 | 94.3 | 4.2 | 98.0 |
| 1.8 | 94.4 | 4.3 | 98.1 |
| 1.9 | 94.5 | 4.4 | 98.3 |
| 2.0 | 94.7 | 4.5 | 98.4 |
| 2.1 | 94.9 | 4.6 | 98.6 |
| 2.2 | 95.0 | 4.7 | 98.7 |
| 2.3 | 95.1 | 4.8 | 98.9 |
| 2.4 | 95.3 | 4.9 | 99.0 |
| 2.5 | 95.5 | 5.0 | 99.2 |
| 2.6 | 95.6 | 5.1 | 99.3 |
| 2.7 | 95.8 | 5.2 | 99.5 |
| 2.8 | 95.9 | 5.3 | 99.8 |
| 2.9 | 96.0 | 5.4 | 99.8 |
| 3.0 | 96.2 | 5.5 | 99.9 |
| 3.1 | 96.3 |  |  |
| 3.2 | 96.5 |  |  |
| 3.3 | 96.6 |  |  |
| 3.4 | 96.8 |  |  |

From this recording, it appears overall that a fluctuation in purity of 0.15% is manifested by a fluctuation of 0.1° C in the crystallization temperature.

For the continuous analysis of the crystallization point of benzene, the extent of measurement corresponds to 2.5° C to 5.5° C, namely to a purity of 95.5 to 99.9%. Since the defined limit corresponds to 1/100 of the length of measurement, it is 0.3° C. According to the method of the invention, the repeatability in measured purity is 0.05% and the response time with a momentary variation in purity of 1% is about 15 minutes.

According to the method of the present invention, it is possible to carry out continuous analyses of the crystallization points of other aromatic substances such as paraxylene or orthoxylene, as well as any substances whose crystallization temperatures are situated between −30° C and ambient temperature.

Figure 4:
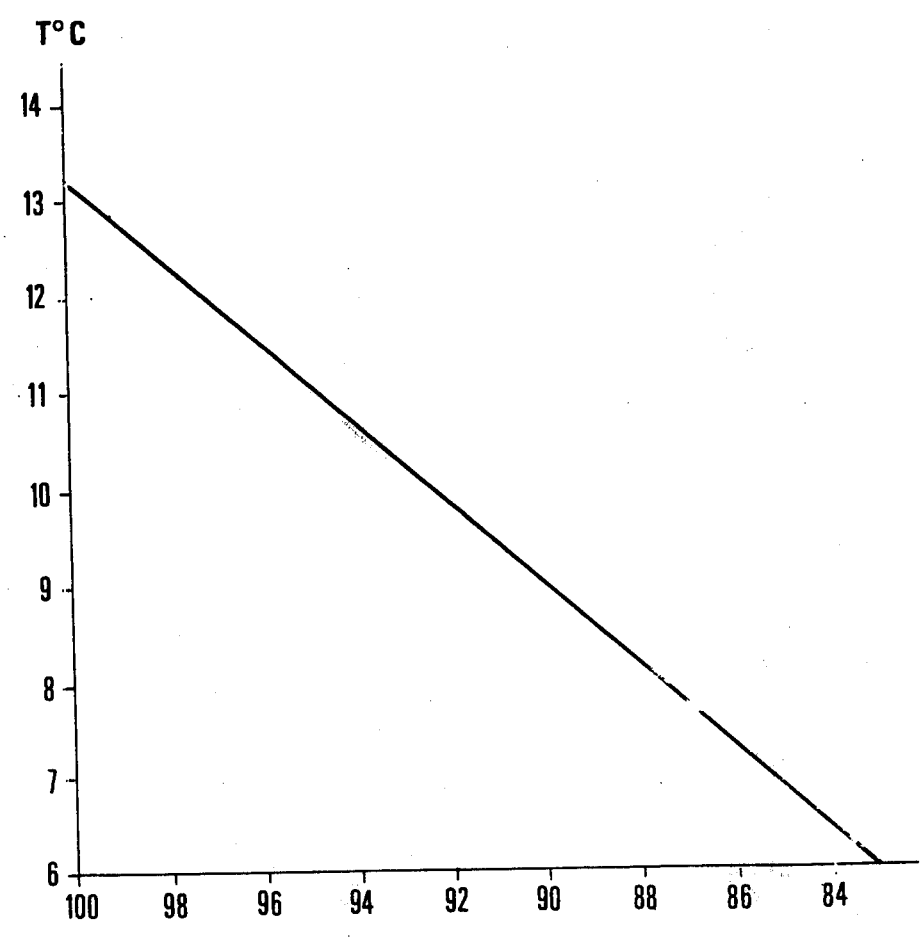
FIG. 4 is a graph showing the temperature/purity relationship for paraxylene.

In FIG 4, is shown the crystallization temperature in °C as a function of the % of purity of paraxylene, this curve having been calculated from the cryoscopic constants.

Below, there is given in Table II the crystallization points recorded by the method according to the invention, as well as the % purity of paraxylene.

TABLE II

| Crystallization point °C | % paraxylene | Crystallization point °C | % paraxylene | Crystallization point °C | % paraxylene |
|---|---|---|---|---|---|
| 11.20 | 94.93 | 11.50 | 95.65 | 11.80 | 96.38 |
| 11.21 | 94.95 | 11.51 | 95.67 | 11.81 | 96.41 |
| 11.22 | 94.98 | 11.52 | 95.70 | 11.82 | 96.43 |
| 11.23 | 95.00 | 11.53 | 95.72 | 11.83 | 96.46 |
| 11.24 | 95.02 | 11.54 | 95.74 | 11.84 | 96.48 |
| 11.25 | 95.05 | 11.55 | 95.77 | 11.85 | 96.51 |
| 11.26 | 95.07 | 11.56 | 95.80 | 11.86 | 96.53 |
| 11.27 | 95.10 | 11.57 | 95.82 | 11.87 | 96.56 |
| 11.28 | 95.12 | 11.58 | 95.84 | 11.88 | 96.58 |
| 11.29 | 95.14 | 11.59 | 95.87 | 11.89 | 96.61 |
| 11.30 | 95.17 | 11.60 | 95.89 | 11.90 | 96.63 |
| 11.31 | 95.19 | 11.61 | 95.91 | 11.91 | 96.65 |
| 11.32 | 95.22 | 11.62 | 95.94 | 11.92 | 96.68 |
| 11.33 | 95.24 | 11.63 | 95.96 | 11.93 | 96.70 |
| 11.34 | 95.26 | 11.64 | 95.99 | 11.94 | 96.73 |
| 11.35 | 95.29 | 11.65 | 96.01 | 11.95 | 96.75 |
| 11.36 | 95.31 | 11.66 | 96.04 | 11.96 | 96.78 |
| 11.37 | 95.34 | 11.67 | 96.06 | 11.97 | 96.80 |
| 11.38 | 95.36 | 11.68 | 96.09 | 11.98 | 96.83 |
| 11.39 | 95.38 | 11.69 | 96.11 | 11.99 | 96.85 |
| 11.40 | 95.41 | 11.70 | 96.14 | 12.00 | 96.88 |
| 11.41 | 95.43 | 11.71 | 96.16 | 12.01 | 96.90 |
| 11.42 | 95.46 | 11.72 | 96.18 | 12.02 | 96.93 |
| 11.43 | 95.48 | 11.73 | 96.21 | 12.03 | 96.95 |
| 11.44 | 95.50 | 11.74 | 96.23 | 12.04 | 96.98 |
| 11.45 | 95.53 | 11.75 | 96.26 | 12.05 | 97.00 |
| 11.46 | 95.55 | 11.76 | 96.28 | 12.06 | 97.02 |
| 11.47 | 95.58 | 11.77 | 96.30 | 12.07 | 97.05 |
| 11.48 | 95.60 | 11.78 | 96.33 | 12.08 | 97.07 |
| 11.49 | 95.62 | 11.79 | 96.35 | 12.09 | 97.10 |
| 12.10 | 97.12 | 12.40 | 97.85 | 12.70 | 98.60 |
| 12.11 | 97.15 | 12.41 | 97.88 | 12.71 | 98.62 |
| 12.12 | 97.17 | 12.42 | 97.90 | 12.72 | 98.65 |
| 12.13 | 97.20 | 12.43 | 97.93 | 12.73 | 98.67 |
| 12.14 | 97.22 | 12.44 | 97.95 | 12.74 | 98.70 |
| 12.15 | 97.24 | 12.45 | 97.98 | 12.75 | 98.72 |
| 12.16 | 97.27 | 12.46 | 98.00 | 12.76 | 98.74 |
| 12.17 | 97.29 | 12.47 | 98.03 | 12.77 | 98.77 |
| 12.18 | 97.32 | 12.48 | 98.05 | 12.78 | 98.80 |
| 12.19 | 97.34 | 12.49 | 98.07 | 12.79 | 98.82 |
| 12.20 | 97.37 | 12.50 | 98.10 | 12.80 | 98.84 |
| 12.21 | 97.39 | 12.51 | 98.12 | 12.81 | 98.87 |
| 12.22 | 97.42 | 12.52 | 98.15 | 12.82 | 98.90 |
| 12.23 | 97.44 | 12.53 | 98.17 | 12.83 | 98.92 |
| 12.24 | 97.46 | 12.54 | 98.20 | 12.84 | 98.95 |
| 12.25 | 97.49 | 12.55 | 98.23 | 12.85 | 98.97 |
| 12.26 | 97.51 | 12.56 | 98.25 | 12.86 | 99.00 |
| 12.27 | 97.54 | 12.57 | 98.27 | 12.87 | 99.02 |
| 12.28 | 97.56 | 12.58 | 98.30 | 12.88 | 99.05 |
| 12.29 | 97.58 | 12.59 | 98.32 | 12.89 | 99.07 |
| 12.30 | 97.61 | 12.60 | 98.35 | 12.90 | 99.10 |
| 12.31 | 97.63 | 12.61 | 98.37 | 12.91 | 99.12 |
| 12.32 | 97.66 | 12.62 | 98.40 | 12.92 | 99.14 |
| 12.33 | 97.68 | 12.63 | 98.42 | 12.93 | 99.17 |
| 12.34 | 97.70 | 12.64 | 98.45 | 12.94 | 99.20 |
| 12.35 | 97.73 | 12.65 | 98.47 | 12.95 | 99.22 |
| 12.36 | 97.76 | 12.66 | 98.50 | 12.96 | 99.25 |
| 12.37 | 97.78 | 12.67 | 98.52 | 12.97 | 99.27 |
| 12.38 | 97.80 | 12.68 | 98.55 | 12.98 | 99.30 |
| 12.39 | 97.83 | 12.69 | 98.57 | 12.99 | 99.32 |
| 13.00 | 99.35 | 13.10 | 99.60 | 13.20 | 99.85 |
| 13.01 | 99.37 | 13.11 | 99.62 | 13.21 | 99.87 |
| 13.02 | 99.40 | 13.12 | 99.65 | 13.22 | 99.90 |
| 13.03 | 99.42 | 13.13 | 99.67 | 13.23 | 99.92 |
| 13.04 | 99.45 | 13.14 | 99.70 | 13.24 | 99.94 |
| 13.05 | 99.47 | 13.15 | 99.72 | 13.25 | 99.97 |
| 13.06 | 99.50 | 13.16 | 99.75 | 13.26 | 100.00 |
| 13.07 | 99.52 | 13.17 | 99.77 | | |
| 13.08 | 99.55 | 13.18 | 99.80 | | |
| 13.09 | 99.57 | 13.19 | 99.82 | | |

Figure 5:
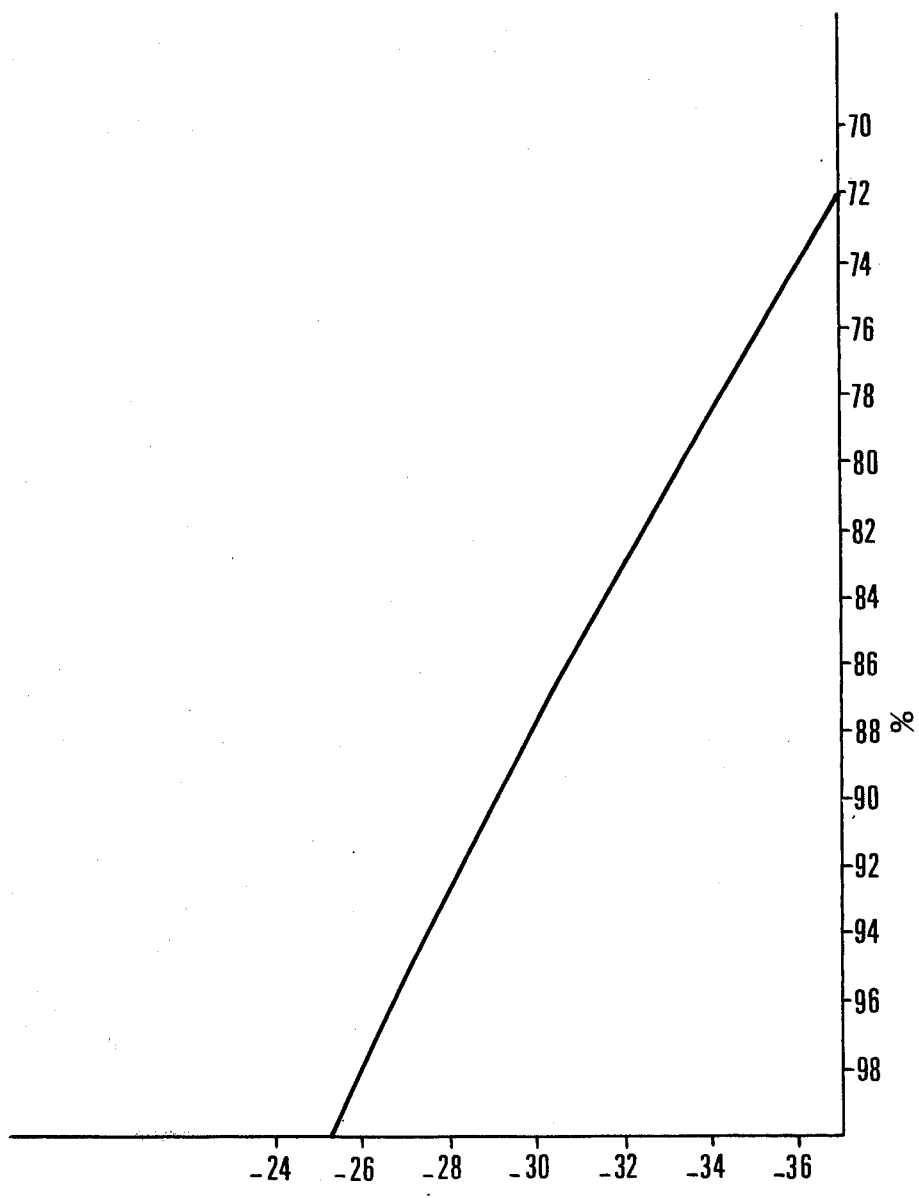
FIG. 5 is a graph showing the temperature/purity relationship for orthoxylene.

In FIG. 5, the crystallization temperature in °C as a function of the percentage purity of orthoxylene is shown by a curve calculated from the cryoscopic constants.

Below, is given in Table III the crystallization points read in a continuous analysis of orthoxylene according to the method of the invention and the percentage purity of the orthoxylene.

TABLE III

PURITY OF THE ORTHOXYLENE AS A FUNCTION OF THE CRYSTALLIZATION POINT

| Crystallization point | % paraxylene |
|---|---|
| −29.0 | 90.2 |
| −29.1 | 90.0 |
| −29.2 | 89.7 |
| −29.3 | 89.5 |
| −29.4 | 89.3 |
| −29.5 | 89.0 |
| −29.6 | 88.8 |
| −29.7 | 88.5 |
| −29.8 | 88.3 |
| −29.9 | 88.1 |
| −30.0 | 87.8 |
| −30.1 | 87.6 |
| −30.2 | 87.3 |
| −30.3 | 87.1 |
| −30.4 | 86.9 |
| −30.5 | 86.5 |
| −30.6 | 86.4 |
| −30.7 | 86.2 |
| −30.8 | 85.9 |
| −30.9 | 85.7 |
| −31.0 | 85.4 |
| −31.1 | 85.2 |
| −31.2 | 85.0 |

The continuous analysis of the crystallization point of an aromatic hydrocarbon enables the purity of the analysed substance to be determined continuously and hence this data to be transmitted directly to a processing system for said hydrocarbon, for example a distillation column, in order to cause the parameters to vary correspondingly.

What I claim is:

1. Method for the continuous automatic analysis of the crystallization point of liquid substances, comprising passing the substance to be analysed through a measuring circuit at a constant flow rate, the temperature therein being maintained at a value sufficiently below the assumed crystallization point of the substance, heating means being provided along the flow path of the liquid substance in said circuit, maintaining the substance in the course of cooling in contact with an isomorphous crystalline material, automatically turning on and off said heating means respectively at two characteristic temperatures, detected by measuring the pressure drop or difference of pressure of the substance at the inlet and at the outlet of the measuring circuit, variations of the pressure drop being effected as a function of temperature, the values thus measured of the pressure drop being utilized as control data for respectively turning on and off the heating means when the temperature of the substance at the outlet reaches one of its two characteristic values, the first corresponding to the crystalline temperature level, whilst the other corresponds to a temperature sufficiently above said crystallization point, and continuously recording the temperature of the substance at the outlet of the circuit, which constitutes a value representing the crysallization point of the substance.

2. Method according to claim 1, wherein said liquid substance is an aromatic hydrocarbon.

3. Method according to claim 2, wherein the liquid substance is benzene, paraxylene or orthoxylene.

4. Apparatus for the continuous automatic analysis of the crystallization point of liquid substances, comprising: a measuring circuit constituted by a capillary tube of stainless steel traversible by said liquid substance, a small volumetric pump included in said circuit to maintain the flow rate of said liquid substance constant, a measuring well containing a cooling liquid bath wherein a large portion of the length of said capillary tube is immersed, the bottom of the well being arranged in the form of a fluid-tight crystals chamber, adapted to contain an isomorphous crystalline material, a short portion of the capillary tube extending through said chamber, aperture means to enable said isomorphous material to be in contact with the substance to be analysed being provided in the portion of the tube situated in said chamber, two electrical leads connected to the inlet and the outlet of the capillary tube in the well, externally to the well, differential pressure-responsive switching means, mounted between the inlet and the outlet of the capillary tube, one said lead being connected directly to the supply whilst the other lead is connected to said differential pressure-responsive switching means, a thermosensitive element positioned at the outlet of the measuring well in the flow path of the liquid substance and a recording device to which said thermosensitive element is coupled.

5. Apparatus according to claim 4, wherein said aperture means comprises a longitudinal opening along a generator of said portion of the tube.

* * * * *